United States Patent [19]
Attar

[11] Patent Number: 4,772,560
[45] Date of Patent: Sep. 20, 1988

[54] LAMINATED WAFER FOR SENSING AND MONITORING EXPOSURE TO GASES

[76] Inventor: Amir J. Attar, 7817 Haymarket Ln., Raleigh, N.C. 27609

[21] Appl. No.: 865,040

[22] Filed: May 19, 1986

Related U.S. Application Data

[63] Continuation-in-part of Ser. No. 798,909, Nov. 18, 1985, abandoned.

[51] Int. Cl.⁴ ..................... G01N 21/03; C01G 37/00
[52] U.S. Cl. .................................. 436/165; 436/177; 436/178; 422/57; 422/58; 422/87; 422/56
[58] Field of Search ........................ 422/56, 57, 58, 59, 422/60, 86, 87; 436/164, 165, 177, 178, 175

[56] References Cited

U.S. PATENT DOCUMENTS

| | | | |
|---|---|---|---|
| 3,399,973 | 9/1968 | Grosskopf | 422/86 X |
| 3,404,962 | 10/1968 | Medlar et al. | 422/86 |
| 3,552,928 | 1/1971 | Fetter | 436/169 X |
| 3,681,027 | 8/1972 | Smith . | |
| 3,847,552 | 11/1974 | Hobgood et al. | 422/86 |
| 3,891,507 | 6/1975 | Breuer . | |
| 3,950,980 | 4/1976 | Braun et al. . | |
| 3,985,017 | 10/1976 | Goldsmith . | |
| 4,205,043 | 5/1980 | Esch et al. . | |
| 4,265,635 | 5/1981 | Kring . | |
| 4,269,804 | 5/1981 | Kring . | |
| 4,271,121 | 6/1981 | Diller et al. . | |
| 4,407,960 | 10/1983 | Tratnyek . | |
| 4,472,353 | 9/1984 | Moore . | |
| 4,478,792 | 10/1984 | McConnaughey et al. | 422/58 X |
| 4,495,291 | 1/1985 | Lawton . | |

FOREIGN PATENT DOCUMENTS 0092101 4/1983 European Pat. Off. .

*Primary Examiner*—Benoit Castel

[57] ABSTRACT

The present invention provides a disposable laminated colorimetric gas monitoring wafer for sensing and monitoring exposure to a selected gas. Opposed gas impermeable layers, such as plastic, generally enclose a carrier medium, such as a sorbent, which carries a color-forming chromophore composition that changes color in response to exposure to a selected gas. A porous, hydrophobic membrane exposed through an opening in one outer plastic layer, overlays the carrying medium and the chromophore composition. Wind and moisture effects are reduced by the porous membrane, and the porous hydrophobic membrane also prevents relative humidity from effecting the color of the chromophore composition.

11 Claims, 1 Drawing Sheet

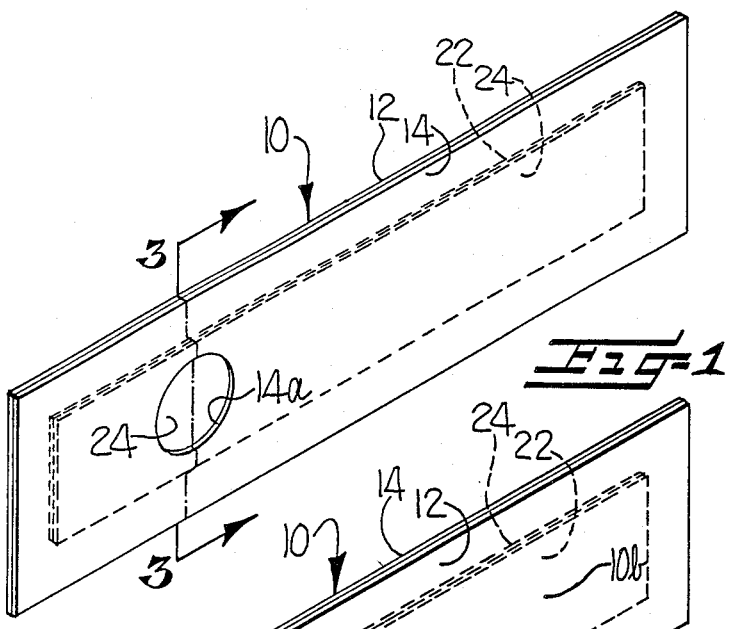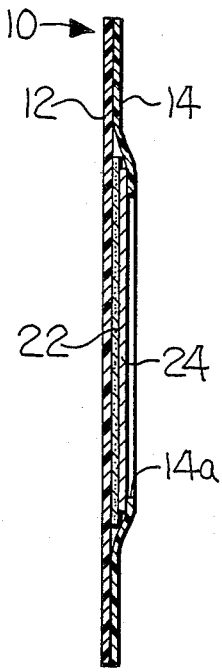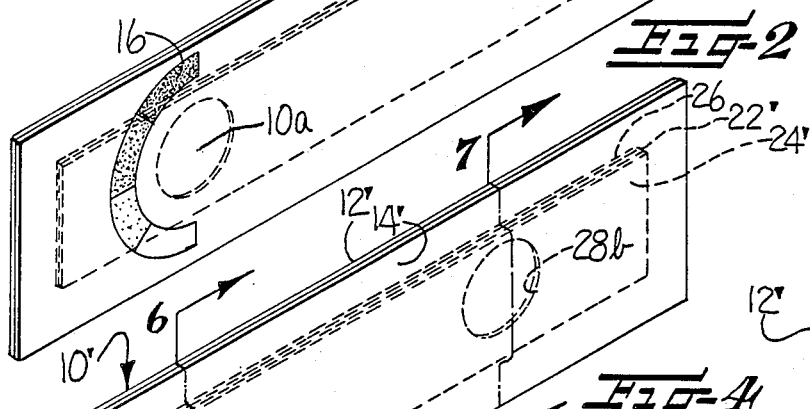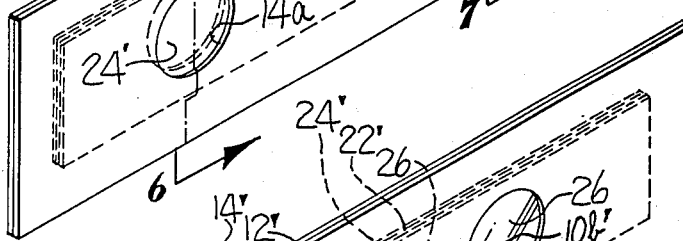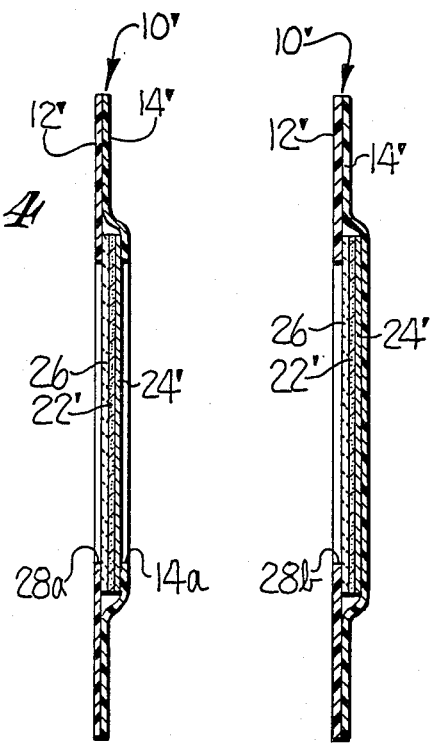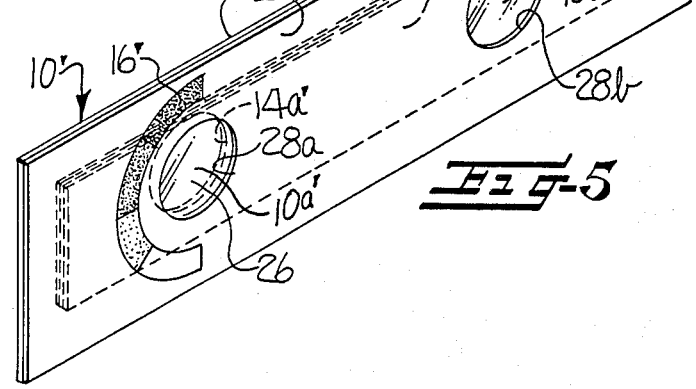

LAMINATED WAFER FOR SENSING AND MONITORING EXPOSURE TO GASES

CROSS REFERENCE TO RELATED APPLICATION

This is a continuation-in-part of copending application Ser. No. 798,909 filed Nov. 18, 1985 now abandoned.

FIELD OF INVENTION

The present invention relates to the field of gas monitoring and dosimetry in general and more particularly to the field of passive dosimetry of hazardous gas concentrations in the air.

BACKGROUND OF INVENTION

Monitoring, sensing and dosimetry of hazardous gas concentrations is extremely important to protect employees of industrial plants, the civilian populations surrounding chemical operations and military personnel. Numerous technologies have been developed for the estimation of the time weighted average gas concentration (TWA), and for the estimation of gas exposure levels. The most important methods are briefly described below:

1. Bubbling of a known quantity of air through an absorbing solution and measuring concentrations of its reaction product in the solution.
2. Passing a known quantity of gas through a column with a solid sorbent which either changes color or is desorbed in a subsequent step and the quantity of the desorbed gas is determined.
3. Adsorbtion of gas onto an activated carbon via a plastic material with large holes and measuring the quantity of adsorbed gas over a known period of time.
4. Absorbtion of gas into a solution and measuring the concentration of its reaction products continuously, e.g., using an electrochemical cell.
5. Measuring the change in the electrical properties of surfaces of solid-state devices after specific gases were adsorbed on them.
6. Measuring the length of a color-stain which develops in an open-end tube filled with a chromophore.
7. Using a diffusion-barrier based passive sampler with subsequent analysis by spectrometric, electrochemical, or chromatographic methods.

Commercially available gas dosimeters employing the techniques described above are generally designed for collecting the fugitive gas sample in the workplace, and then in a subsequent step, the dosimeter is analyzed by an appropriate analytical method or instrument. Typically, each dosimeter is designed for a particular gas, and a different analytical method is required for each gas. Moreover, commerically available gas monitoring devices which employ the above methods are very expensive. Therefore, there has been and continues to be a need for an economical gas monitoring technique which is suitable for a relatively wide range of gas monitoring problems.

A dosimeter with a built-in direct reading capability for giving a semi-quantitative assessment of the exposure level or with features which allow an auxiliary instrument to measure the exposure without further sample preparation would offer tremendous advantage over the above-noted dosimeters and methods in which the gas must be first collected and thereafter analyzed by an auxiliary method or instrument. While several such direct-reading devices have been proposed in the patent literature, they lack the degree of reliability and accuracy needed to make them generally acceptable and useful.

The present invention provides a passive colorimetric gas monitoring device which offers significant advantages over others which have been described in the patent literature or heretofore made available. Smith U.S. Pat. No. 3,681,027 described a passive colorimetric dosimeter for nitrogen dioxide which uses a solid impregnated with a diazotation mixture as a chromophore to detect nitrogen oxide. The dosimeter of Smith is not quantitative because the color reading is affected by the relative humidity and by the local superficial wind velocity. Moreover, the specific formulation used by Smith is not very stable and tends to decompose and forms color upon exposure to ozone, UV light and other reagents.

The passive dosimeters of Esch et al and of Moore (U.S. Pat. Nos. 4,205,043 and 4,472,353, respectively) offer advantages over that of Smith because they provide a reference window for color comparison, which can be used to compensate for the instability of the sensing chromophoric reagent. However, in both cases the color reading will be sensitive to the wind superficial velocity and to the relative humidity.

The dosimeter of McConnaughy (U.S. Pat. No. 4,478,792) offers some advantage over that of the previous two because it uses porous sheets impregnated with the chromophoric reagent to restrict the effect of wind velocity. However, it does not provide a way to compensate for the instability of the chromophoric reagent and the reading is still sensitive to the relative humidity. Other inventions have used diffusion barriers to overcome the effect of wind velocity, e.g., Cadoff and Hodgeron (Anal. Chem., 55 p. 2083-2085, 1983) and in several patents, e.g., Braun et al., U.S. Pat. No. 3,950,980; Goldsmith, U.S. Pat. No. 3,985,017; Kring U.S. Pat. Nos. 4,265,635 and 4,269,804.

The colorimetric gas dosimeters of the prior art have failed to appreciate or recognize that relative humidity almost always influences the color development of the sensing chromophoric reagent. Thus, one of the novelties of this invention is a method and apparatus which can eliminate the effect of the relative humidity as well as that of the air face velocity.

SUMMARY AND OBJECTS OF THE INVENTION

It is therefore an object of the present invention to provide a passive gas dosimeter that is simple in construction, yet highly reliable.

A further object of the present invention is to provide a gas monitoring device which is inexpensive and disposable.

Another object of the present invention is to provide a gas monitoring device in the form of a multilayered wafer including a porous membrane for reducing wind and moisture effects upon the color change.

Another object of the present invention is to provide a gas monitoring device in the form of a multilayered wafer including a film which changes color upon exposure to a specific gas.

Another object of the present invention is to provide a built-in color reference which can be used to compensate for instability of the chromophore.

Yet another object of the present invention is to provide a gas monitoring device of the character referred to above wherein exposure can be quantitatively determined by comparing the color change to a color standard affixed to the wafer or by using an instrument.

Other objects and advantages of the present invention will become apparent from a review of the detailed description of the invention and the accompanying drawings.

The present invention provides a gas monitoring method and apparatus that is inexpensive and is suitable for a wide range of gas monitoring problems. The heart of the present invention is a wafer which consists of several layers, one of which contains a color-forming chromophore composition. The chromophore-containing layer changes color in response to exposure to a specific gas. The color change can be used to monitor the instantaneous gas concentration and/or the cumulative dose of exposure to the gas and subsequently the time-weighted average gas concentration. Quantitative determination can be made by comparing the color change to a color standard or by using an instrument, such as a photometer. Wind and moisture effects are overcome by including in the wafer one or more permeable membranes through which the ambient gas must pass in order to reach the chromophore. At least one of the membranes should be a hydrophobic membrane. The membranes control the response time and sensitivity while preventing the passage of water vapors, and if needed, to remove interfering gases.

More particularly, the colorimetric gas monitoring wafer of the present invention comprises a gas impermeable base; a carrier medium disposed over the base; a color-forming chemical which changes color in response to exposure to a selected gas carried on the carrier medium; a gas impermeable cover secured to the base for encapsulating the carrier medium and the color-forming chemical; an opening formed in the cover for allowing ambient air to enter the wafer and contact the color-forming chemical; a permeable hydrophobic membrane overlying the color-forming chemical and aligned with the opening in the cover so that the ambient air must pass through the membrane to reach the color-forming chemical; and means defining a transparent measurement area on the base located opposite the opening in the cover for viewing the change and color of the color-forming chemical as a result of contact by the ambient air. The wafer may be additionally provided with means defining a transparent reference area on the base located remote from the opening in the cover and in an area where the color-forming chemical is encapsulated and free from contact with the ambient air for viewing any change in color of the color-forming chemical which is not a result of contact by the ambient air.

BRIEF DESCRIPTION OF THE DRAWINGS

FIG. 1 is a plan view of the top side of a gas monitoring wafer in accordance with the present invention;

FIG. 2 is a plan view of the opposite side of the gas monitoring wafer of FIG. 1, that side being referred to as the bottom side;

FIG. 3 is an enlarged sectional view taken along the line 3—3 in FIG. 1;

FIG. 4 is a plan view of the top side of a gas monitoring wafer in accordance with a second embodiment of the invention;

FIG. 5 is a plan view of the opposite or bottom side of the wafer of FIG. 4;

FIG. 6 is an enlarged sectional view taken along the line 6—6 in FIG. 4; and

FIG. 7 is an enlarged sectional view taken along the line 7—7 in FIG. 4.

DESCRIPTION OF THE INVENTION

Referring now to the drawings, the gas monitoring wafer of the present invention is shown therein in FIG. 1 and indicated generally by the numeral 10. The wafer 10 includes a base 12 and a cover 14. Base 12 comprises a generally flat, rectangular gas impermeable layer constructed preferably from a plastic material such as polyester, polyethylene, or the like. The base 12 may be comprised of a transparent plastic laminate formed by one or more layers of plastic material. For example, base 12 may comprise an outer plastic film of approximately 10 mils, laminated to a second plastic support layer of approximately 40 mils by a polyethylene adhesive.

Overlying the base 12 is a layer containing a color-forming chemical which changes color in response to exposure to a selected gas. Preferably, and as illustrated, the color-forming chemical is disposed on a carrier medium 22. The carrier medium may comprise a thin strip of paper or paper-like material, or a thin layer of a sorbent such as silica or alumina. In the preferred embodiment illustrated, the carrier medium comprises a thin paper-like strip in which there is dispersed a granular sorbent material such as silica or alumina. The sorbent functions to receive and carry the color-forming chemical which is utilized to indicate exposure to a specific gas.

As best seen in FIG. 3, the carrier medium 22 is of smaller lateral and longitudinal dimensions than the base 12 such that peripheral portions of the base project beyond the carrier medium 22. Overlying the carrier medium 22 is a gas impermeable cover 14. As illustrated, the cover 14 is laminated to the base 12 along the peripheral edge portions so that the carrier medium 22 and the color-forming chemical carried thereby are totally encapsulated and sealed within the wafer 10. The cover 14 is formed of a gas impermeable plastic material, preferably a transparent plastic. As best seen in FIG. 1, an opening 14a is formed in the cover 14 to allow ambient air to enter the wafer and contact the color-forming chemical in the area located beneath the opening.

A porous membrane layer 24 is disposed over the carrier medium 22 and specifically over the portion of carrier medium which is under the opening 14a in the cover 14. The purpose of the membrane layer is to reduce errors caused by the effects of wind and moisture on the chromophore. The presence of a permeable membrane overlying the chromophore reduces the effect of the wind superficial velocity. In the illustrated embodiment, a single membrane is used. However, several membranes of the same or of differing properties may be used to adjust the gas flux and/or selectivity. Additionally, a layer of filter material, formed for example of filter paper or other suitable permeable material, may be inserted parallel to the membrane or membranes to screen or trap impurities and thereby increase the selectivity to a particular desired gas.

It is important, however, that at least one of the membranes in the membrane layer 24 be a hydrophobic membrane. Hydrophobic membranes are much more permeable to non-polar gases than to polar gases, and thus serve as a barrier to water vapor while allowing comparatively free passage of non-polar gases. The membrane permeability to a specific gas is determined by the pore size, the pore shape, the thickness of the membrane, and by the nature of the active sites on the membrane. These factors may be selectively varied, as desired, in order to tailor the characteristics of the monitoring wafer for a particular gas and to assist in screening out other gases which may interfere with the chromophore reading. Hydrophobic membranes useful in the present invention may be prepared from hydrophobic materials such as polypropylene, polytetrafluoroethylene (PTFE), other fluoropolymers. Alternatively, non-hydrophobic membranes may be treated by suitable hydrophobic agents to render the membrane hydrophobic. For example, a hydrophilic cellulose nitrate membrane may be rendered hydrophobic by contacting the membrane with a reactive silicon compound, e.g. a halosilane such as trimethylchlorosilane, a siloxane such as methyl-trimethoxysilane, or a silazane such as hexamethyldi-silazane. The reactive silicone compound reacts with the hydrophilic functional groups of the membrane, e.g. hydroxyl, amino and acido groups, to form hydrophobic silane groups, thus rendering the membrane hydrophobic. Alternatively, the membrane may be rendered hydrophobic by treating it with a hydrophobic polymer, e.g. dimethyl polysiloxane.

The bottom side of the wafer 10 includes two side-by-side color areas 10a and 10b. Color area 10a is located opposite the opening 14a in the cover and serves as a measurement area where the changing color of the chromophore, which is visible through the transparent base 10a, indicates the exposure level to the selected gas. The color area 10b is a sealed reference color area which is used to compensate for any drift or change in the color of the chromophore which is not due to exposure to the ambient gases. The actual dose of exposure is proportionate to the difference in the color between the reference area 10b and the measuring area 10a.

Thus, the user can easily estimate the cumulative exposure or dosage at any time by simply comparing the color developed on the measuring area 10a with the color of the reference area 10b. To further assist in making a visual reading, the wafer is provided with a color standard chart 16 attached to the base 10 adjacent to the measurement area 10a to allow the user to compare the color developed in the measuring area 10a with preselected colors on the color chart which are representative of selected exposure levels.

A more accurate quantitative assessment of the exposure can be obtained through the use of a suitable optical instrument, such as a photometer or spectrometer. Since the reference area 10b is located in side-by-side relation with the measurement area 10a, a double-beam photometer can be conveniently used to assess the color difference between the reference area and the measuring area.

The particular color varying chemical composition or element of wafer 10 will vary depending upon the particular gas that the wafer 10 is designed to sense. For example, a wafer designed to sense and monitor $NO_2$ exposure levels could be provided with the following chromophore composition:

0.25 grams 2-Napthyl amine
0.15 grams Citric Acid
10 ml Methanol
3 ml 1 Normal NaOH
1 gram Glycerol 40 micro liter droplets are used to produce the reference and the measuring spots on the wafer.

The above chromophore composition is spotted on both sides of the carrying medium or sorbent 22 before cover 14 is laminated to base 12. After spotting, the methanol solvent is allowed to dry before cover 14 is laminated to base 12.

Examples of other chromophore compositions which may be used for other gases are disclosed in U.S. Pat. Nos. 3,574,552; 3,852,034; 4,205,043; 4,258,000; 4,348,358, 4,478,792, and 4,495,291.

The embodiment of the invention illustrated in FIGS. 4 and 7 is similar in most respects to that previously described in connection with FIGS. 1–3. To avoid repetitive description, elements of this embodiment which correspond to those previously described in connection with the embodiment of FIGS. 1–3 will be identified, wherever applicable, by the same reference characters with prime notation (') added.

Referring now in more detail to FIGS. 4 and 5, the wafer 10' differs primarily over the previous embodiment by the presence of a rigid transparent supporting layer 26 underlying the carrier layer 22'. The rigid supporting layer suitably comprises a transparent glass plate. Additionally, and as best seen in FIG. 5, the base 12' has openings or holes 28a, 28b formed therein through which the glass plate is exposed to form the measurement area and the reference area. The hole 28a is located directly opposite the opening 14a' in cover 14', while the opening 28b is at a remote location where the color-forming chemical is completely encapsulated within the wafer and thus not exposed to the ambient air. The use of the transparent optical glass plate 26 as a reinforcing backing within the wafer 10' facilitates direct optical reading of the optical density from the back of the wafer with the use of an appropriate instrument.

EXAMPLE 1: A TYPICAL WAFER STRUCTURE

An example of the gas monitoring wafer 10 of the present invention includes a base 12 constructed of a layer of transparent 10 mil polyester film approximately 25 mm wide and 75 mm long. A layer of 20 mil polyester with a 40 mil layer of 300 mesh activated silica is attached to the base 12 as a carrying medium or sorbent 22. A chemical formulation including a chromophore is applied to the carrying medium or sorbent 22. As noted above, the composition of the chemical formulation will depend upon the specific gas to be detected. A membrane 24 constructed of 0.45 micron cellulose nitrate covers a square of approximately ½ inch by ⅜ inch area of the silica. Cover 14 comprises a layer of 10 mil polyester film thermally adhered to base 12 so as to encapsulate the remaining elements. An opening of approximately 10 mm by 15 mm is formed in the cover 14 to permit gas diffusion through the membrane 24.

The wafer 10 may be attached to a person's clothing so that is is carried at all times. The sensed gas in ambient air can diffuse through membrane 24 and come in contact with the chromophore composition on the carrier 22. If the air contains any concentrations of the selected gas, the chromophore composition will change colors to indicate such. The color change, of course, may be clearly seen through base 12, which is transparent. The amount of exposure to the gas may be determined by comparing the color developed in the measurement area to color standards which may be placed on base 12 adjacent the color change area of the wafer 10. Once the amount of exposure is determined, the wafer 10 may be disposed.

EXAMPLE 2: A TYPICAL WAFER WITH A TRANSPARENT PLATE BACKING STRUCTURE

The wafer with a transparent plate backing includes a plate 26, typically of a high quality glass with a thickness of 0.15–0.5 mm, which is inserted between the carrier medium 22' and the bottom plastic layer 12'. The bottom also contains one large or two smaller viewing holes 28a 28b which allow direct color reading of the wafer. FIG. 4 shows the back side of a wafer when two holes are used. Typical holes in the plastic may be $\frac{3}{4}$ inches in diameter and $\frac{1}{2}$ inches apart.

EXAMPLE 3: EFFECT OF THE RELATIVE HUMIDITY

Most formulations for color detection of hydrogen sulfide use lead acetate as the chromophore, since it develops a brown color upon exposure to sulfides.

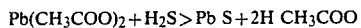

$$Pb(CH_3COO)_2 + H_2S > Pb\ S + 2H\ CH_3COO$$

This reaction is ionic and therefore very sensitive to relative humidity. The formulation set forth in Table 1 below is capable of detecting a dose of several ppb.hr of $H_2S$; however, its sensitivity is a strong function of the relative humidity.

Table 1

1 gram glycerine
1 gram carbowax 1000
10 ml methanol
3 ml of 1 molar Pb $(CH_3COO)_2$ solution A silica-based sorbent was dipped in the mixture, dried in the air for 20 minutes, and used as the chromophore carrier. A 45 micron nitrocellulose membrane was treated with a hydrophobic silazation reagent to render the membrane hydrophobic by immersing the membrane in a solution consisting of 10:50 parts by volume of hexamethyldisilazane in dry heptane at 40° C. for 5 to 10 minutes, followed by air drying. A treated membrane and an untreated membrane (control) were incorporated into wafers and subjected to dry and humid gases containing ppm $H_2S$ for equal periods of time. The color of the measurement area was measured photometrically, and the results are reported in Table 2.

TABLE 2

| Membrane | Dry Gas | Humid Gas (60% RH) | Difference |
|---|---|---|---|
| Treated | 1670 | 1595 | 115 |
| Untreated | 1175 | 1820 | 647 |

The Reduction of the Sensitivity of the Wafer to the Relative Humidity (photometer readings)

It will be seen from Table 2 that humid air has much less effect on the color reading when a treated (hydrophobic) membrane is used as compared to an untreated membrane which is not hydrophobic.

In the drawings and specification, there has been set forth a preferred embodiment of the invention, and although specific terms are employed, they are used in a generic and descriptive sense only and not for purposes of limitation.

That which is claimed is:

1. A colorimetric gas monitoring wafer for sensing and measuring gas concentrations and/or cumulative exposure dose of a selected gas comprising
   a gas impermeable base;
   a color-forming chemical which changes color in response to exposure to a selected gas disposed over said base;
   a gas impermeable cover secured to said base for encapsulating said color-forming chemical;
   a carrier medium disposed over said base and encapsulated by said cover, and wherein said color-forming chemical is carried on said carrier medium;
   an opening formed in said cover for allowing ambient air to enter the wafer and contact said color-forming chemical;
   a gas permeable hydrophobic membrane which is a barrier to water vapor while allowing comparatively free passage of non-polar gases overlying said color-forming chemical and aligned with said opening so that the ambient air must pass through the membrane to reach said color-forming chemical; and
   means defining a transparent measurement area on said base located opposite said opening in said cover for viewing the change in color of said color-forming chemical as a result of contact by the ambient air.

2. The gas monitoring wafer of claim 1 wherein said carrier medium comprises a sorbent.

3. The gas monitoring wafer of claim 2 wherein said sorbent is selected from the group consisting of silica and alumina.

4. The gas monitoring wafer of claim 1 wherein said carrier medium comprises a thin, paper-type material.

5. The gas monitoring wafer of claim 1 additionally comprising means defining a transparent reference area on said base located remote from said opening and in an area where the color-forming chemical is encapsulated and free from contact with the ambient air for viewing any change in color of said color-forming chemical which is not a result of contact by the ambient air.

6. The gas monitoring wafer of claim 1 additionally including a comparative color chart carried by said base adjacent to said measurement area and including reference colors indicative of predetermined levels of exposure to the specific gas for comparison to the color in the indicator viewing area.

7. The gas monitoring wafer of claim 1 including at least one additional permeable membrane disposed adjacent to and alongside said permeable hydrophobic membrane.

8. The gas monitoring wafer of claim 1 including a layer of filter material disposed adjacent to and alongside said permeable hydrophobic membrane to trap impurities present in the ambient gas and thereby increase the selectivity of the reading.

9. A colorimetric gas monitoring wafer for sensing and measuring gas concentration and/or cumulative exposure dose of a selected gas, comprising
   a gas impermeable transparent base;
   a carrier medium disposed over said base;
   a color-forming chemical which changes color in response to exposure to a selected gas carried on said carrier medium;
   a gas impermeable cover secured to said base for encapsulating said carrier medium and said color-forming chemical;

an opening formed in said cover for allowing ambient air to enter the wafer and contact said color-forming chemical;

a gas permeable hydrophobic membrane which is a barrier to water vapor while allowing comparatively free passage of non-polar gases overlying said carrier medium and the color-forming chemical thereon and aligned with said opening so that the ambient air must pass through the membrane to reach said color-forming chemical;

a portion of said transparent base located opposite said opening in said cover defining a transparent measurement area for viewing the change in color of said color-forming chemical as a result of contact by ambient air; and a portion of said transparent base located remote from said opening and in an area where the color forming chemical is encapsulated and free from contact with the ambient air defining a transparent reference area for viewing any change in color of said color-forming chemical which is not a result of contact by the ambient air.

10. A colorimetric gas monitoring wafer for sensing and measuring gas concentrations and/or cumulative exposure dose of a selected gas, comprising a gas impermeable base;

a rigid optically transparent support layer overlying said base;

a carrier medium disposed over said support layer;

a color-forming chemical which changes color in response to exposure to a selected gas carried on said carrier medium;

a gas impermeable cover secured to said base for encapsulating said carrier medium, said color-forming chemical disposed thereon, and said rigid optically transparent support layer;

an opening formed in said cover for allowing ambient air to enter the wafer and contact said color-forming chemical;

a gas permeable hydrophobic membrane which is a barrier to water vapor while allowing comparatively free passage of non-polar gases overlying said carrier medium and the color-forming chemical thereon and aligned with said opening so that the ambient air must pass through the membrane to reach said color-forming chemical;

an opening provided in said base opposite the opening in said cover, and serving to expose the underlying transparent support to view so as to form a measurement area for viewing the change in color of said color-forming chemical as a result of contact by the ambient air; and an opening formed in said transparent base at a location remote form said opening in the cover and being in an area where the color-forming chemical is encapsulated and free from contact with the ambient air and serving to expose the underlying transparent support to view for viewing any change in color of the color-forming chemical which is not a result of contact by the ambient air.

11. A method for determining the amount of exposure to a specific gas comprising placing a carrier medium on a thin, wafer-like base;

applying to said carrier medium a color-forming chemical which changes colors in response to exposure to said specific gas;

covering at least part of said chemical with a gas permeable hydrophobic membrane which is a barrier to water vapor while allowing comparatively free passage of nonpolar gases;

affixing a cover, having an opening, to said base so as to encapsulate said carrier medium, color-forming chemical and membrane therebetween to prevent gas diffusion to the carrier medium except through said membrane;

allowing ambient air to pass through said opening and said membrane so that gas concentrations in the air will contact said color-forming chemical causing the same to change colors; and evaluating the resulting color of said color-forming chemical to determine the exposure of said specific gas.

* * * * *